United States Patent [19]

Muroi et al.

[11] Patent Number: 4,749,458

[45] Date of Patent: * Jun. 7, 1988

[54] FREE-FLOW ELECTROPHORETIC SEPARATION METHOD AND APPARATUS THEREFOR

[75] Inventors: Katsumi Muroi; Kosai Hiratsuka; Shoji Yoshinaga, all of Kudamatsu; Toji Nakatsui, Hikari; Chikao Oda, Kudamatsu; Kiyoshi Fujiwara, Kudamatsu, all of Japan

[73] Assignee: Hitachi, Ltd., Tokyo, Japan

[*] Notice: The portion of the term of this patent subsequent to Oct. 6, 2004 has been disclaimed.

[21] Appl. No.: 20,773

[22] Filed: Mar. 2, 1987

Related U.S. Application Data

[63] Continuation of Ser. No. 760,940, Jul. 31, 1985, Pat. No. 4,698,142.

[30] Foreign Application Priority Data

Jul. 31, 1984 [JP] Japan .................................. 59-158724
Sep. 26, 1984 [JP] Japan .................................. 59-199582

[51] Int. Cl.[4] ........................ G01N 27/28; G01N 27/26
[52] U.S. Cl. .................................. 204/182.3; 204/180.1; 204/183.2; 204/183.3; 204/182.6; 204/299 R; 204/301

[58] Field of Search ............... 204/180.1, 182.3, 183.2, 204/183.3, 299 R, 301, 182.6

[56] References Cited

U.S. PATENT DOCUMENTS

| | | | |
|---|---|---|---|
| 2,878,178 | 3/1959 | Bier | 204/182.3 |
| 3,989,613 | 11/1976 | Gritzner | 204/301 |
| 4,155,831 | 5/1979 | Bhattacharya | 204/299 R |
| 4,172,774 | 10/1979 | Moeglich | 204/182.3 |
| 4,465,583 | 8/1984 | Lovegrove | 204/299 R |

*Primary Examiner*—John F. Niebling
*Assistant Examiner*—Ben C. Hsing
*Attorney, Agent, or Firm*—Antonelli, Terry & Wands

[57] ABSTRACT

The invention discloses a free-flow electrophoretic separation method and apparatus for separating charged substances such as proteins, cells, and the like, by electrophoresis, which comprises supplying a mixed solution containing the charged substances to be separated, which are dissolved in a separation buffer, into a separation chamber, circulating the mixed solution inside the separation chamber, applying a d.c. voltage to the mixed solution to cause the electrophoresis of the charged substances and to separate them, and withdrawing the charged substances thus separated from outlets disposed at one and the other end of the separation chamber.

2 Claims, 7 Drawing Sheets

FREE-FLOW ELECTROPHORETIC SEPARATION METHOD AND APPARATUS THEREFOR

This is a continuation of application Ser. No. 760,940, filed July 31, 1985, now U.S. Pat. No. 4,698,142.

BACKGROUND OF THE INVENTION

1. Field of the Invention

This invention relates to technique for separating charged substances such as proteins, nucleic acids, cells, and the like, and more particularly to a free-flow electrophoretic separation method and apparatus therefor which separates and extracts charged substances by utilizing electrophoresis.

2. Description of the Prior Art

An electrophoretic separation method, a membrane separation method and liquid chromatography are known conventionally as methods of separating and purifying charged substances such as proteins, nucleic acids, cells, and the like. The membrane separation method separates proteins by means of its pore size. Though capable of continuous processing, this method involves the problem that the separability of proteins is low. Liquid chromatography passes proteins to be separated through a carrier packed column and separates them. Though the separability is high, this method is not suitable for mass-processing on an industrial scale because the operation is carried out in batch-wise. The electrophoretic separation method separates and purifies proteins in an electric field by use of the difference of charge quantities of the proteins. This method can be classified into a carrier electrophoretic separation method using a carrier such as a gell, and a free-flow electrophoretic separation method which effects separation in a free flow without using a carrier. The carrier electrophoretic separation method is conducted batch-wise, and hence the free-flow electrophoretic separation method is suitable for mass-processing on an industrial scale.

The free-flow electrophoretic separation method is disclosed, for example, in Kurt Hannig's "Electrophoresis", 3, p.p. 235–243, 1982, West Germany. This method will be described in further detail.

A mixture of proteins to be separated is charged continuously into a separation buffer that flows down at a constant speed across an electric field inside an electrophoretic chamber. Since each protein has a different charge quantity, its electrophoretic mobility is also different in the electric field. Therefore, each protein is deflected and separated while it flows down in the separation buffer in conjunction with the flowing velocity of the separation buffer. It can thus be understood that this method can continuously separate the proteins and hence is effective for the separation and purification of the proteins on an industrial scale.

In order to improve the separability by this method, it is important to always keep constant the flowing velocity of the separation buffer inside the separation chamber. However, since a current is caused to flow through the separation buffer, joule heat occurs necessarily, and this heat causes convection in the separation buffer and hence, turbulence of the flow of the separation buffer. In consequence, the separability of the proteins drops. To obviate this problem, it has been necessary for a conventional free-flow electrophoretic separation apparatus to control the temperature and flowing velocity of the separation buffer to a level of accuracy as high as ±0 2%. To accomplish this object, the separation chamber must be miniaturized in a thin flat sheet form, and this in turn results in the practical problem that the processing quantity is too small to conduct the separation on a large industrial scale.

U.S. Pat. No. 3,989,613 discloses an electrophoretic separation apparatus having a construction which comprises two electrophoretic chambers divided by a boundary membrane consisting of a semipermeable membrane, electrodes and electrode chambers disposed on both sides of the boundary membrane, cooling chambers each disposed between each electrode chamber and each electrophoretic chamber, and liquid inlets and outlets disposed at the upper and lower portions of each of the two electrophoretic chambers. The separation of the charged substances is effected by this apparatus in the following manner. A separation buffer is supplied from the upper inlet of one of the two electrophoretic chambers, while a separation buffer which contains the two charged substances to be separated are mixed is supplied from the upper inlet of the other electrophoretic chamber. A d.c. voltage is then applied across both electrodes for separation. The separation buffer and the solution of the charged substances flow down inside the electrophoretic chambers, and some of the charged substances permeate through the boundary membrane at the center into the other electrophoretic chamber from the electrophoretic chamber on the supply side due to electrophoresis, while the other flows down through the electrophoretic chamber on the supply side. The two charged substances are then withdrawn from the lower outlets of the respective electrophoretic chambers. In this apparatus, too, the thickness of each electrophoretic chamber is extremely small in order to eliminate any adverse influences of the joule heat caused by the application of the d.c. voltage. For this reason, the processing quantity is small and the apparatus can not be adapted to mass processing.

SUMMARY OF THE INVENTION

The present invention is directed to provide a free-flow electrophoretic separation method and apparatus which can increase the processing quantity of charged substances to be separated.

It is another object of the present invention to provide a free-flow electrophoretic separation method and apparatus which has high separation accuracy of charged substances and which can separate the charged substances in large quantities.

In accordance with a preferred embodiment of the present invention, a mixed solution of charged substances to be separated and a separation buffer is supplied into a separation chamber and is circulated inside the separation chamber, a d.c. voltage is applied to the circulating flow of the mixed solution to separate the charged substances, and the separated solution from which the charged substances are separated is withdrawn from the separation chamber.

In accordance with another embodiment of the present invention, there is provided a free-flow electrophoretic separation apparatus which comprises a separation chamber, a pair of electrodes for applying a d.c. voltage to a solution inside the separation chamber, an inlet for supplying a mixed solution of charged substances to be separated and a separation buffer into an electrophoretic separation chamber, outlets for withdrawing separated solutions, disposed close to one of the pair of electrodes at one end side of the electrophoretic separation chamber and close to the other of the pair of the electrodes at the other end side of the electrophoretic separation chamber, respectively, and means for circulating the mixed solution inside the electrophoretic separation chamber.

These and other objects and features of the present invention will become more apparent from the following description to be taken in conjunction with the accompanying drawings.

DESCRIPTION OF THE PREFERRED EMBODIMENTS

Hereinafter, the present invention will be described in further detail with reference to the accompanying drawings.

Figure 1:
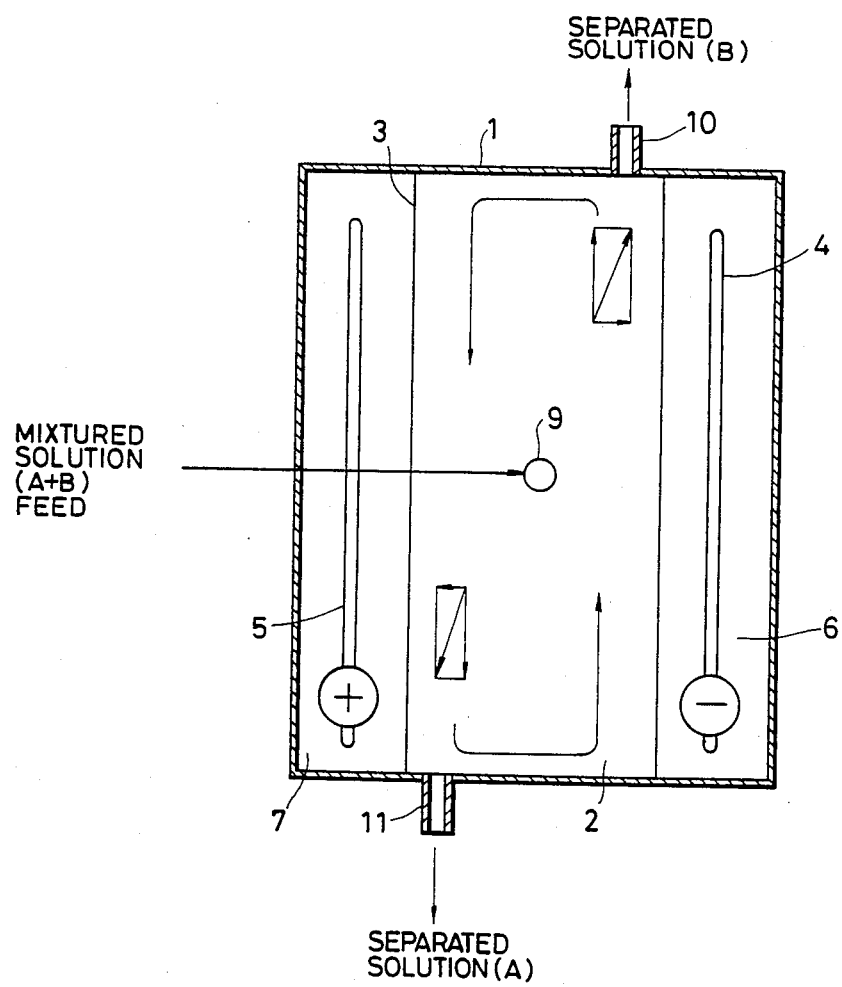
FIG. 1 is a schematic view useful for explaining the principle of the present invention.

First of all, the principle of the present invention will be described with reference to FIG. 1. An electrophoretic separation apparatus shown in the drawing includes an electrophoresis cell 2 disposed inside a separation chamber 1, and electrode cells 6 and 7 disposed on both sides of the electrophoresis cell 2. Outlets 10 and 11 for withdrawing solutions separated by electrophoresis (or separated solutions) are disposed at the lower and upper end portions of the electrophoresis cell 2 close to the electrode cells 5 and 6, respectively. A mixed solution of charged substances to be separated such as proteins and a separation buffer is supplied into the electrophoresis cell 2 through an inlet 9. Electrodes 4 and 5 for applying a d.c. voltage to the mixed solution in the electrophoresis cell 2 are disposed in the electrode cells 6 and 7, respectively. The electrophoresis cell 2 and the electrode cells on both sides are separated by membranes 3. The mixed solution is continuously supplied from the inlet into the electrophoresis cell 2, and is circulated in a predetermined direction inside the electrophoresis cell 2 by suitable circulation means not shown in the drawing. A d.c. voltage is applied across the electrodes 4 and 5 to generate an electric field.

It will now be assumed that the charged substances to be separated are two kinds of proteins A and B, and the isoelectric points $PI_A$ and $PI_B$ of these proteins A and B satisfy the relation $PI_A < PI_B$. In this case, the pH of the separation buffer is prescribed to be an intermediate value between $PI_A$ and $PI_B$. Under this condition, the charged substance A is charged negative (−) while the charged substance B is charged positive (+). It will also be assumed that the mixed solution supplied into the electrophoresis cell is circulated in a direction represented by an arrow in the drawing to form a circulating flow. The charged substances A and B in the mixed solution gradually move towards the electrodes while being circulated. In other words, the protein A which is charged negative moves to the positive electrode 7 due to the circulating flow, and after all, to the position close to the positive electrode 5 (that is, close to the outlet 11) at the lower end of the electrophoresis cell 2. The charged protein B charged positive moves towards the negative electrode 4 due to the circulating flow, and to the position close to the negative electrode (that is, close to the outlet 10) at the upper end of the electrophoresis cell 2. Thus, a separated solution in which the protein B is concentrated is obtained from the upper outlet 10 while a separated solution in which the protein A is concentrated is obtained from the lower outlet 11.

As described above, the present invention circulates forcedly the mixed solution of the separation buffer and the charged substances to be separated inside the electrophoresis cell, and separates the charged substances by this circulating flow in cooperation with the movement (electrophoresis) of the charged substances due to the application of the d.c. voltage.

Some preferred embodiments of the invention based upon the principle described above will now be described in detail.

Figure 2:
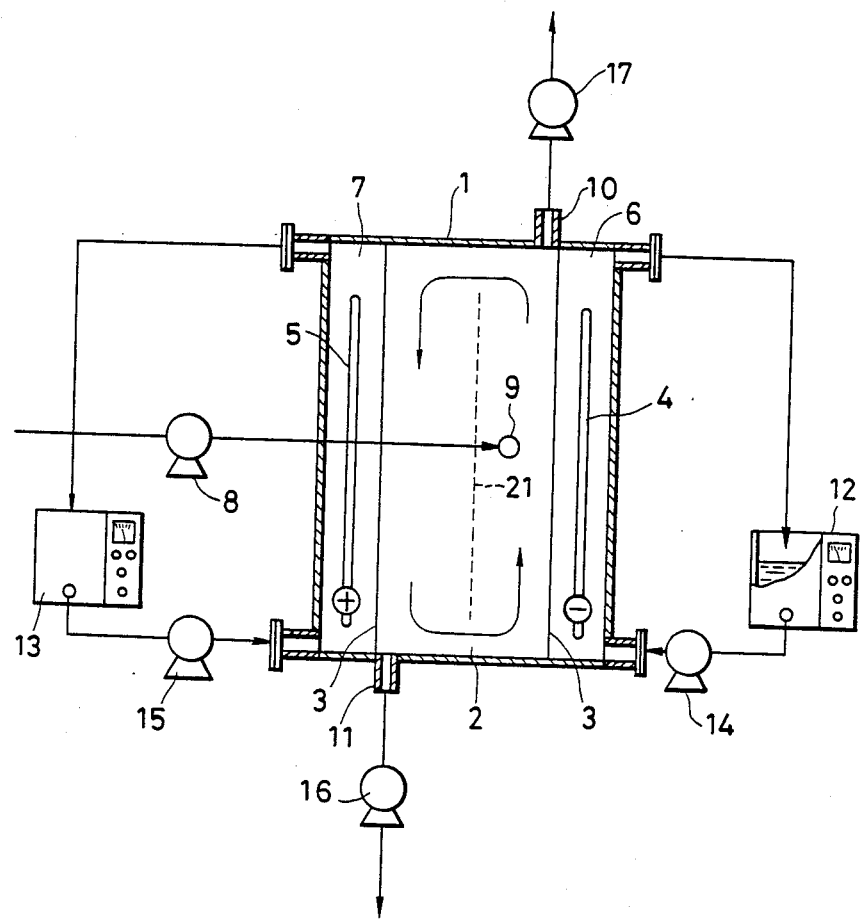
FIG. 2 is a schematic view showing one embodiment of the present invention.

FIG. 2 shows a first embodiment of the present invention. In the drawing, a separation chamber 1 is shown divided by membranes 3, thereby forming an electrophoresis cell 2 and electrode cells 6 and 7. The membrane 3 can pass therethrough small particles such as ions in the separation buffer (e.g., $Na^+$, $K^+$, $H^+$, $OH^-$) and electricity, but does not pass therethrough large particles having a large molecular weight such as proteins. A dialytic membrane for dialysis, an ion exchange membrane, cellophane, or the like, is suitable as the membrane 3. Electrodes 4 and 5 are disposed in the electrode cells 6 and 7, respectively. A mixed solution of the separation buffer and proteins A and B is led to an inlet 9 by a pump 8, and is supplied into electrophoresis cell 2 through the inlet 9. To accomplish the continuous processing, the mixed solution is continuously supplied from the inlet 21 during the operation of the apparatus.

Electrode buffers that are adjusted to predetermined temperature are supplied to the electrode cells 6 and 7, respectively. In other words, the electrode buffers are adjusted to the respective temperature set values by temperature controllers 12 and 13, and are supplied into the respective electrode cells 6 and 7 by pumps 14 and 15. After passing through the electrode cells 6 and 7, these electrode buffers are returned to the respective temperature controllers 12, 13, thus forming circulating paths. Here, the temperature set values $T_1$ and $T_2$ of the temperature controllers 12 and 13 are set so as to satisfy the relation $T_1 > T_2$. As a result, the temperature of the electrode buffer (which is about $T_1$) supplied into the electrode cell 6 and the temperature of the electrode buffer (which is about $T_2$) supplied to the electrode cell 7 have a temperature difference $\Delta T$ ($=T_1-T_2$). If $T_1$ and $T_2$ are selected in such a fashion that this temperature difference $\Delta T$ becomes sufficiently great, considerably great temperature non-uniformity occurs in the mixed solution inside the electrophoresis cell 2. In other words, a temperature distribution in this case is such that the mixed solution close to the electrode cell 6 has a high temperature, and the mixed solution close to the electrode cell 7, a low temperature. As a result, the mixed solution inside the electrophoresis cell 2 circulates due to thermal convection. The circulating direction is represented by an arrow in the drawing.

A guide member 21 is disposed at the center of the electrophoresis cell 2 to make more reliable the formation of the circulating flow. It has openings or notches at its upper and lower portions so as not to disturb the circulating flow. The guide member 21 consists of a porous material having pores or gaps sufficient enough to permit the passage of proteins.

A d.c. voltage is applied across the electrodes 4 and 5 together with the circulation of the mixed solution in the electrophoresis cell 2. Assuming that the mixed solution containing the proteins A and B is continuously supplied to the electrophoresis cell, the proteins A and B flow and move with the circulating flow of the mixed solution, and move to the negative and positive electrodes 5 depending upon the polarity of charge. As a result, the proteins separated by movement are condensed at the portions close to the outlet 10 and close to the outlet 11 of the electrophoresis cell 2. These separated solutions are withdrawn from the outlets 10 and 11 by pumps 16 and 17, respectively, thereby providing the separated proteins A and B.

An example when charged substances were separated by use of the apparatus shown in FIG. 2 is given below.

Separation example by the apparatus shown in FIG. 2:

The charged substances to be separated were as follows:

| myoglobin (horse) | isoelectric point | 7.1–7.3 |
|---|---|---|
| lysozyme (chicken egg) | " | 11.0–11.4 |

Boric acid buffer whose pH was adjusted to 9.0 by NaOH was used as the separation buffer. The mixed solution supplied from the inlet was prepared by dissolving the charged substances in the boric acid buffer. The concentration of each charged substance was 0.25 g/l. The volume of the electrophoresis cell 2 was 60 cm$^3$, and a cellulose acetate membrane was used as the separation membrane 3. The temperatures of the electrode buffers (boric acid buffers) in both electrode cells 6 and 7 on both sides of the electrophoresis chamber 2 were adjusted to 5° C. and 15° C., respectively, with a temperature difference of 10° C. by the temperature controllers 12 and 13. The electrode buffers were supplied into the electrode cells 6 and 7 at a flowing velocity of 200 ml/min, and the separated solutions were withdrawn from the outlets 10 and 11 at a rate of 0.5 ml/min. A constant current of 0.05 A (voltage of 450 V) was caused to flow through the electrodes to conduct continuously electrophoresis. The separated solutions were analyzed by high-performance liquid chromatography. As a result, the separation reached the steady state at about 60 minutes after the feed of power, and myoglobin and lysozyme in the separated solution withdrawn from the outlet 10 were 0.38 g/l and 0.11 g/l, respectively, while myoglobin and lysozyme in the separated solution withdrawn from the outlet 11 were 0.10 g/l and 0.38 g/l, respectively. Incidentally, these data were when the guide member 21 was not disposed. 1 mm, porosity 32%) was used as the guide member 21 and notches of 6 cm$^2$ were formed at the upper and lower ends of the guide member 21, the following result was obtained. In this case, the experimental condition was the same as described above.

Myoglobin and lysozyme in the separated solution withdrawn from the outlet 10 were 0.40 g/l and 0.10 g/l, respectively, while myoglobin and lysozyme in the separated solution withdrawn from the outlet 11 were 0.09 g/l and 0.39 g/l, respectively. A better result could thus be obtained by use of the guide plate 21.

Figure 3:
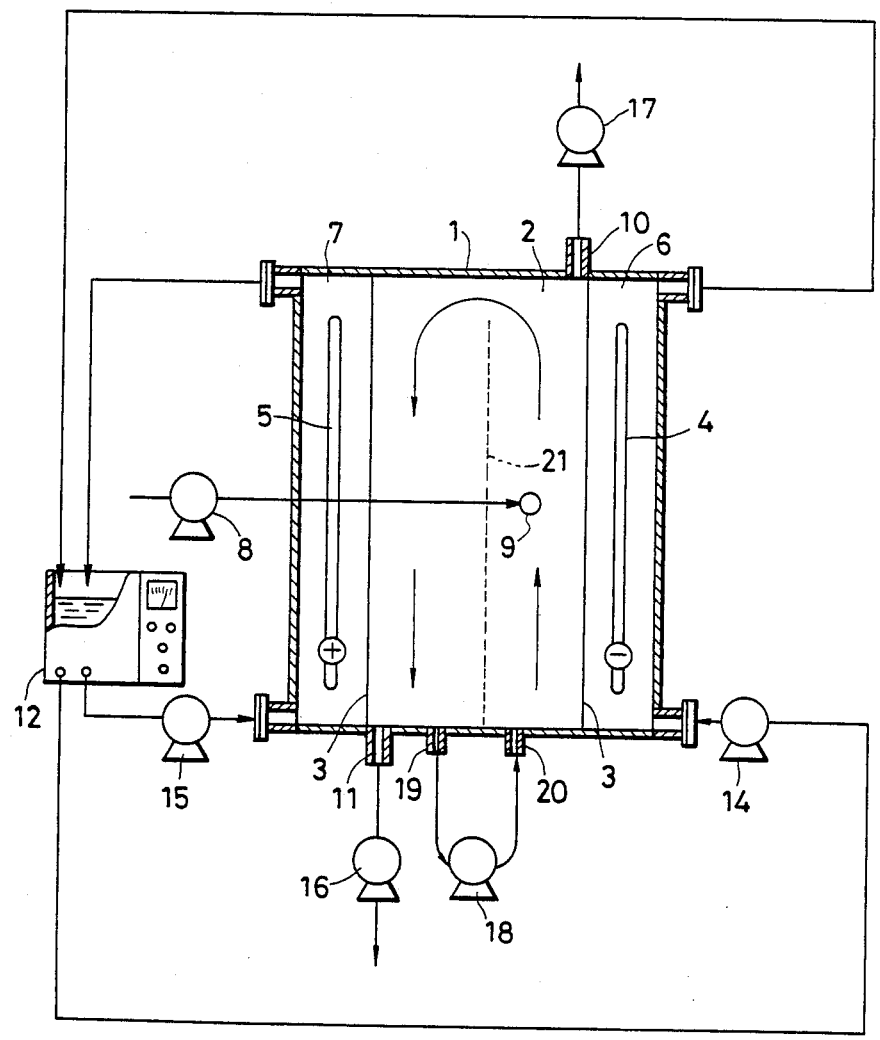
FIG. 3 is a schematic view showing another embodiment of the present invention.

Next, another embodiment of the present invention will be described with reference to FIG. 3. The apparatus shown in FIG. 3 is substantially the same as one shown in FIG. 2 except that the circulation means for circulating the mixed solution in the electrophoresis cell is different. In the apparatus shown in FIG. 2, the temperature of the electrode buffers supplied to the electrode cells on both sides of the electrophoresis cell were different from each other so that a temperature distribution was formed in the mixed solution in the electrophoresis cell, and a circulating flow was formed by thermal convection. In the apparatus shown in FIG. 3, on the other hand, the mixed solution in the electrophoresis cell 2 is forcedly circulated by a pump. As shown in FIG. 3, circulating nozzles 19 and 20 as well as a circulating pump 18 are disposed, the mixed solution is withdrawn from the nozzle 19 and is supplied to the circulating pump 18, and the mixed solution discharged from the pump 18 is returned into the electrophoresis cell 2 from the nozzle 20, thereby forming the circulating flow of the mixed solution.

In the apparatus shown in FIG. 3, the mixed solution containing two kinds of proteins A and B is supplied from the inlet 9, and while the mixed solution in the electrophoresis chamber 2 is being circulated by driving the pump 18, a d.c. voltage is applied across the electrodes, whereupon the proteins A and B are separated to the outlets 10 and 11 due to the circulating flow in cooperation with electrophoresis. Incidentally, the temperatures of the electrode buffers to be supplied to the electrode cells 6 and 7 are controlled to the same temperature by the temperature controller 12. It is of course possible to provide a temperature difference between both electrode buffers to be supplied to the electrode cells in the same way as in the apparatus shown in FIG. 2 to effect the circulation due to thermal convection, and to form the necessary circulating flow by the conjoint use of the circulating pump 18. In the apparatus shown in FIG. 3, the pump 18 is disposed outside the electrophoresis cell 2 in order to form the stable circulating flow. However, the circulating flow of the mixed solution may be formed by disposing a jet pump inside the electrophoresis cell 2.

The following is an example when charged substances were separated using the apparatus shown in FIG. 3.

Example of separation by the apparatus shown in FIG. 3:

The charged substances to be separated and the separation buffers were the same as those used in FIG. 2. The other condition was also the same.

The mixed solution was supplied by the pump 8 from the inlet 9 at a flow velocity of 1.0 ml/min, and the separated solutions were withdrawn from the outlets 10 and 11 at a rate of 0.5 ml/min. The circulating flow by the circulating pump 18 was 1.0 ml/min, and was circulated counter-clockwise as shown in the drawing. A constant current of 0.05 A (450 V) was applied across the electrodes to continuously effect electrophoresis. As a result, under the steady state, myoglobin and lysozyme were 0.37 g/l and 0.12 g/l in the separated solution withdrawn from the upper outlet 10, respectively, and they were 0.11 g/l and 0.36 g/l in the separated solution withdrawn from the lower outlet 11, respectively. Incidentally, these data were when the guide member 21 was not disposed.

When a filtration membrane (pore diameter 2.5 μm) was used as the guide member 21 and a 6 cm² notch was formed at the upper end of the membrane for circulating the mixed solution in the electrophoresis cell, the following result could be obtained. Myoglobin and lysozyme in the separated solution withdrawn from the outlet 10 were 0.42 g/l and 0.08 g/l, respectively, and they were 0.07 g/l and 0.41 g/l, respectively, in the separated solution withdrawn from the outlet 11.

Next, still another embodiment of the invention will be described with reference to FIG. 4. In the apparatus shown in FIG. 4, the separation chamber 1 is of a cylindrical type, though the separation chamber 1 in the foregoing embodiments is of a flat plate type. In the apparatus shown in FIG. 4, the electrode 5 is disposed at the center of this cylindrical separation chamber 1 with the other electrode 4 being disposed around the peripheral portion of the separation chamber. The interior of the separation chamber 1 is divided concentrically into three portions by the membrane 3, that is, the electrode cell 6, the electrophoresis cell 2 and the electrode cell 7 at the center, from the peripheral portion of the separation chamber 1 in order named. The electrode 4 is disposed in the electrode cell 6, and the electrode 5 forming a pair with the former is disposed in the electrode cell 7. A plurality of electrodes 4 on the peripheral side are disposed around the inner circumference of the chamber 1. The inlet 9 is disposed at the drum portion of the separation chamber 1 and is sufficiently long to reach the electrophoresis cell 2. A plurality of inlets 9 are also disposed in the circumferential direction. A plurality of upper outlets 10 are disposed at positions close to the center electrode 5 inside the cylindrical electrophoresis cell 2. A plurality of lower outlets 11 are disposed at positions close to the electrodes 4 on the peripheral side in the electrophoresis cell 2. The membrane consists of such a material that permits the passage of small particles such as ions in the separation buffer and electricity but not large particles such as proteins. The temperature controllers 12 and 13 control the temperatures of the electrode buffers to be supplied to the electrode cells 7 and 6 to the respective values. The set values $T_1$ and $T_2$ of these temperature controllers 12 and 13 satisfy the relation $T_1 > T_2$. As a result, the temperature of the electrode buffer supplied to the electrode cell 7 is higher than the temperature of the electrode buffer supplied to the electrode cell 6, so that non-uniformity of temperature occurs in the mixed solution in the electrophoresis cell 2, and the temeprature of the mixed solution is higher close to the electrode cell 7 than close to the electrode cell 6. Therefore, the mixed solution in the electrophoresis cell 2 turns to a circulating flow due to thermal convection as represented by dotted arrows in the drawing. A d.c. voltage is applied across the electrodes 4 and 5, and the mixed solution containing the charged substances to be separated is continuously fed into the electrophoresis cell 2. The charged substances are separated in the electrophoresis cell 2 by the interaction of the electrophoretic migration and the circulating flow, and the separated solutions are withdrawn from the outlet 10 by the pump 17 and from the outlet 11 by the pump 16.

It will be now assumed that the charged substances to be separated are proteins A and B whose isoelectric points $PI_A$ and $PI_B$ satisfy the relation $PI_A > PI_B$. The separation buffer has a pH which is in advance adjusted to an intermediate value between these values. Under such a condition, the protein A is charged negative and the protein B, positive. Therefore, the protein A moves towards the positive electrode 5, and the protein B towards the negative electrode 4. Due to this migration and the movement caused by the circulating flow, the separated solution containing a greater proportion of the protein A is withdrawn from the outlet 10, and the separated solution containing a greater proportion of the protein B is withdrawn from the outlet 11. The direction of convection becomes opposite if the temperature of the electrode buffer to be supplied to the electrode cell 6 is higher than that of the electrode buffer to the electrode cell 7. In such a case, too, the separation of the charged substances is possible. Alternatively, the polarity of the voltage to be applied across the electrodes may be reversed.

Figure 4:
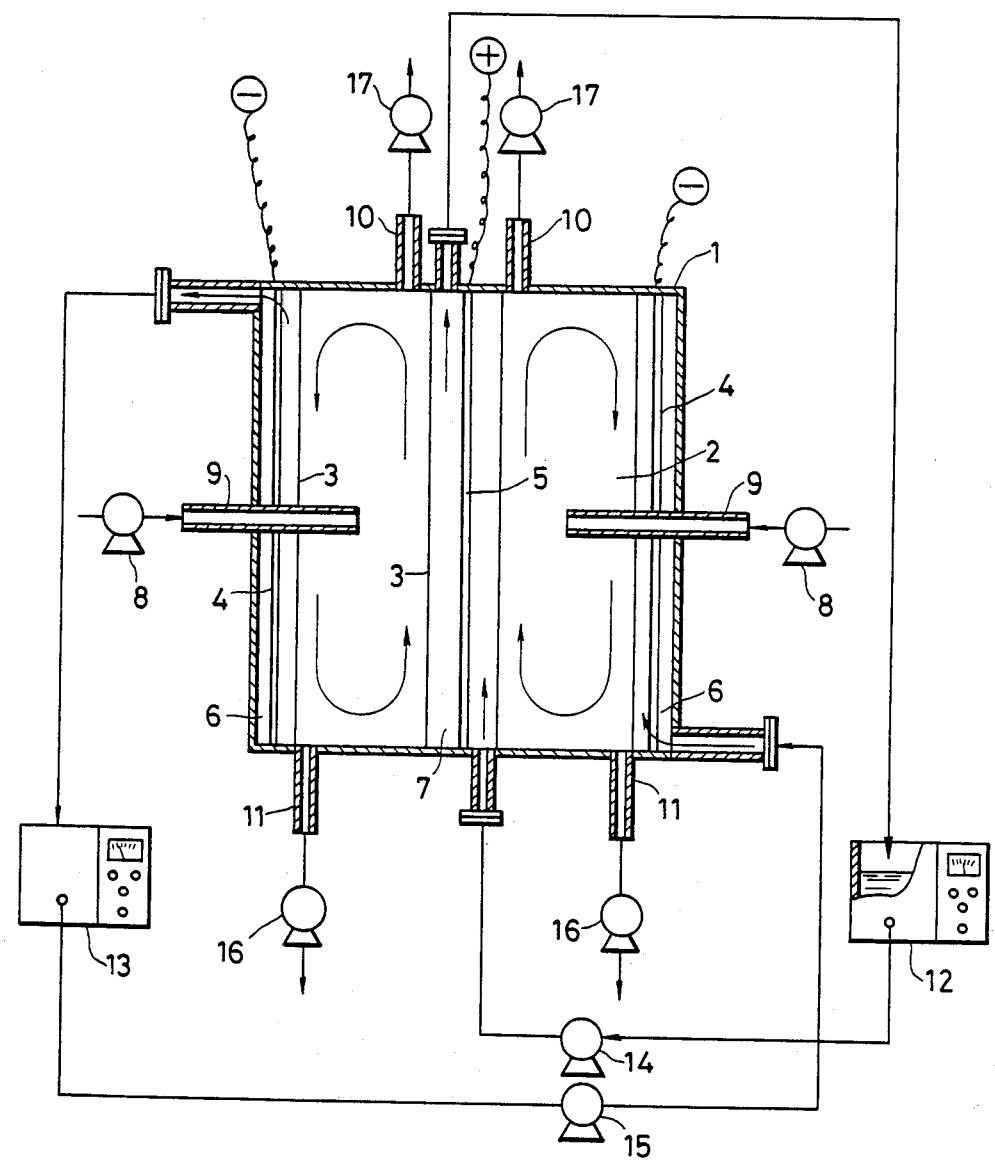
FIG. 4 is a schematic view showing still another embodiment of the present invention.

The following is an example when the charged substances were separated by use of the apparatus shown in FIG. 4.

Example of separation by the apparatus shown in FIG. 4:

The charged substances to be separated and the separation buffer were the same as those in the apparatus shown in FIG. 2. The electrode buffer was controlled to 15° C. by the temperature controller 12, and was supplied to the electrode cell 7 by the pump 14 at a rate of 300 ml/min. On the other hand, the electrode buffer to be supplied to the electrode cell 6 was controlled to 5° C. by the temperature controller 13, and was supplied to the electrode cell 6 by the pump 15 at a rate of 300 ml/min.

The mixed solution containing the charged substances was fully charged into the electrophoresis cell 2, and the circulating flow of the mixed solution was formed by the temperature difference of the electrode buffers to be supplied to the electrode cells. Two each outlets 10 and 11 were disposed. The separated solution was withdrawn from the two outlets 10 by the pump 17 at a rate of 1.0 ml/min, while it was withdrawn from the two outlets 11 by the pump 16 at a rate of 1.0 ml/min. The mixed solution was supplied at a rate of 2.0 ml/min into the center of the electrophoresis cell 2 from the two inlets 9 by the pump 8. A cellulose acetate film was used as the separation membrane 3. The membrane 3 had an area of 471 cm² on the inside and 785 cm² on the outside.

A constant current 0.1 A (320 V) was supplied between the electrodes 5 and 4 to conduct continuous processing. As a result, myoglobin and lysozyme in the separated solution withdrawn from the upper outlet 10 were 0.35 g/l and 0.14 g/l, respectively, and they were 0.13 g/l and 0.32 g/l in the separated solution withdrawn from the lower outlet 11.

Figure 5:
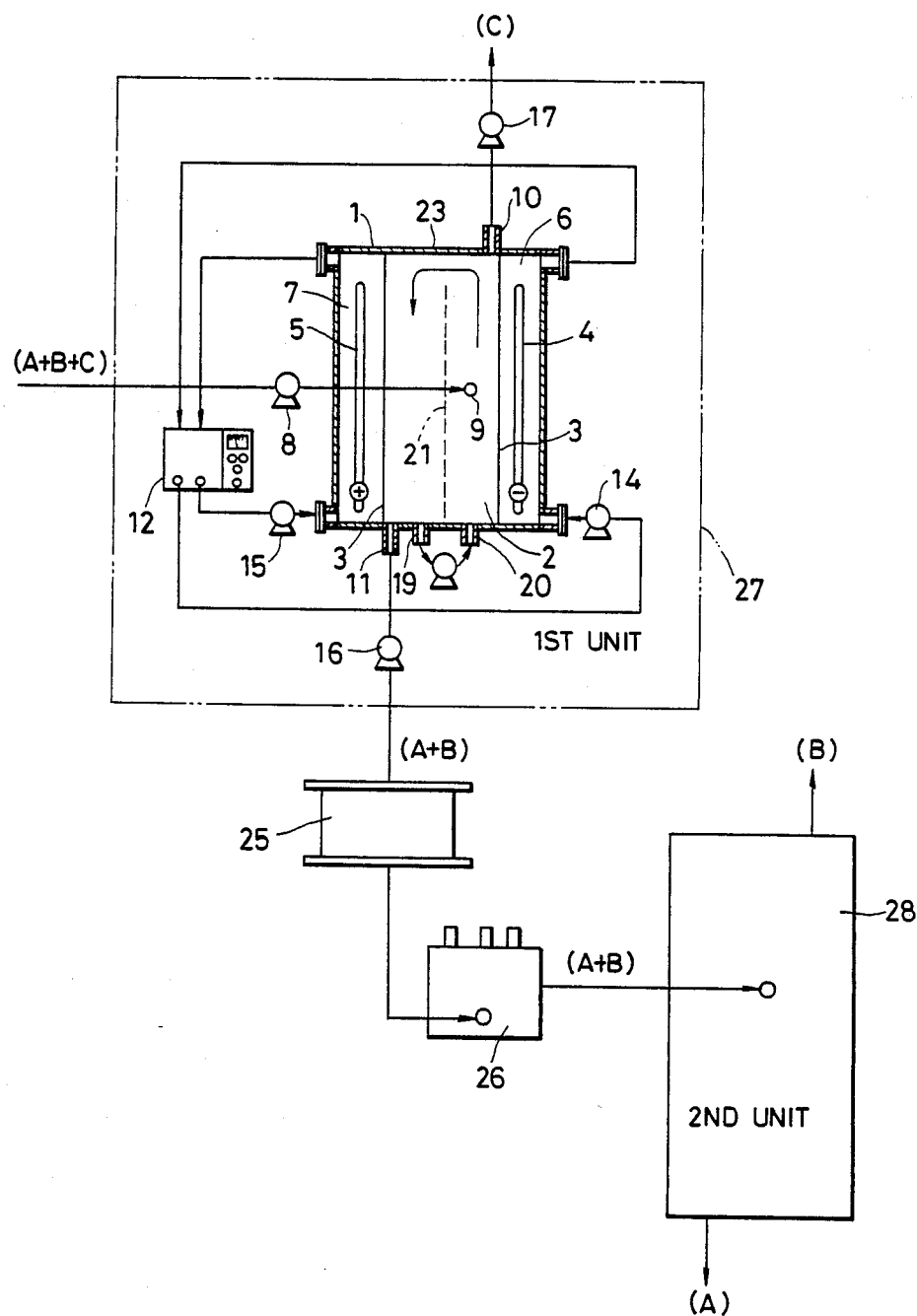
FIG. 5 is a schematic view showing still another embodiment of the present invention.

The foregoing embodiments use only one set of the free-flow electrophoretic separation apparatus. Though only one set of the apparatus can separate the charged substances, three or more kinds of charged substances can be separated if a plurality of sets of these free-flow electrophoretic separation apparatuses are connected in series. FIG. 5 shows still another embodiment of the present invention, in which two electrophoretic separation apparatuses are connected in series in order to separate three kinds of charged substances. In the drawing, the electrophoretic separation apparatus 27 (which will be hereinafter called the "first unit") has the same construction as the apparatus shown in FIG. 3. The electrophoretic separation apparatus 28 (which will be hereinafter called the "second unit") has exactly the same construction as the first unit. The outlet 11 of the first unit 17 is connected to the inlet of the second unit 28 through a buffer convertor 25 and a pH adjuster 26. Therefore, the separated solution withdrawn from the outlet 11 of the first unit 27 by the pump 16 is subjected to the buffer conversion and to the pH adjustment, and is then supplied to the electrophoresis cell of the second unit 28 from its inlet.

The buffer convertor 25 removes only the salts contained in the withdrawn separated solution to prepare a solution containing the charged substances, and then adds desired buffer or buffers to the separated solution. Thus, the buffer in the separated solution is exchanged. The pH adjuster 26 adjusts the pH of the separated solution after buffer exchange to a level suitable for the separation processing in the second unit 28 by use of an acid or an alkali. Therefore, the separated solution leaving the pH adjuster 26 is suitable for the processing in the second unit 28.

Now, it will be assumed that the proteins to be separated are three kinds of proteins A, B and C. A mixed solution containing the proteins A, B and C to be separated and the separation buffer is supplied into the electrophoresis cell 2 of the first unit 27 from its inlet 9. The separation buffer used for the first buffer is adjusted in advance so that it charges the protein C positive and the proteins A and B negative. The mixed solution in the electrophoresis cell 2 is forcedly circulated inside the electrophoresis cell 2 by the circulation pump 18, thereby forming a circulating flow. A d.c. voltage is applied across the electrodes 4 and 5. As a result, the protein C moves towards the negative electrode 4 because it is charged positive. Due to the movement caused by the circulating flow and to the movement towards the negative electrode 4, the protein C is separated in the proximity of the outlet 10. The proteins A and B move towards the positive electrode 5 because they are charged negative. Due to the movement caused by the circulating flow and to the movement towards the positive electrode 5, the proteins A and B are separated in the proximity of the outlet 11. Therefore, a separated solution containing a great proportion of the protein C (concentrated solution) is obtained from the outlet 10, while a separated solution containing a great proportion of the proteins A and B is obtained from the outlet 11.

The separated solution containing a great proportion of the proteins A and B, that is withdrawn by the pump 16, is passed through the buffer exchanger 25 and the pH adjuster 26 so that a separation buffer suitable for separating the proteins A and B and a mixed solution containing the proteins A and B can be obtained. The second unit 28 receives this mixed solution and separates the proteins A and B from each other. It will be assumed that the protein A is charged negative and the protein B, positive. Then, the separated solution containing a great proportion of the protein A is obtained from the lower outlet 11, while the separated solution containing a great proportion of the protein B is obtained from the upper outlet 10. In this manner, three kinds of proteins A, B and C are separated from one another.

The following is an example when the charged substances were separated by use of the apparatuses shown in FIG. 5.

Example of separation by the apparatuses shown in FIG. 5:

The charged substances to be separated were as follows:

| | |
|---|---|
| albumin (bovine) | isoelectric point PI = 4.9 |
| myoglobin (horse) | isoelectric point PI = 7.1~7.3 |
| lysozyme (chicken egg) | isoelectric point PI = 11.0~11.4 |

A boric acid buffer (pH=9.0, electroconductivity—40 ms/m) was used as the separation buffer in the first unit 27. The three kinds of charged substances listed above were dissolved at a rate of 0.25 g/l in the separation buffer boric acid buffer) to prepare a mixed solution. This mixed solution was supplied into the electrophoresis cell 2 of the first unit 27 through its inlet 9. The feeding velocity was 2.0 ml/min. A circulating flow having a flow velocity of 2.0 ml/min was formed by the circulation pump 18, and a d.c. of 0.1 A (voltage=210 V) was applied between the electrodes 4 and 5. The withdrawing rates of the separated solution withdrawn from the upper outlet 10 and the lower outlet 11 of the first unit 27 were 1.0 ml/min, respectively.

The electrode buffers to be supplied to the electrode cells 6 and 7 were the same as the separation buffer, were adjusted to 5° C. by the temperature controller 12 and were supplied at a rate of 200 ml/min by the pumps 14 and 15, respectively. As a result, a separated solution containing a large proportion of lysozyme was obtained from the upper outlet 10 of the first unit 27, while a separated solution containing a large proportion of myoglobin and albumin was obtained from the lower outlet 11 of the first unit 27.

Next, the separated solution obtained from the outlet 11 of the first unit was supplied to the buffer exchanger 25 consisting of a gel filter and a buffer supplier so as to exchange the separation buffer with the phosphoric acid buffer. Subsequently, the solution was adjusted to pH=6.0 by the pH adjuster 26. After being adjusted in this manner, the solution was supplied to the second unit 28 at a rate of 2.0 ml/min. The operation was carried out in the second unit 28 in the same way as in the first unit 27. The current supplied between the electrodes in the second unit 28 was 0.05 A (450 V), and the other condition was the same as in the first unit. As a result, a separated solution containing a large proportion of myoglobin was obtained from the upper outlet 10 (not shown) of the second unit 28, while a separated solution containing a large proportion of alubumin was obtained from the lower outlet 11 (not shown). The result can be summarized as follows.

0.07 g/l of albumin, 0.06 g/l of myoglobin and 0.42 g/l of lysozyme were obtained from the separated solution withdrawn from the upper outlet 10 of the first unit 27.

0.01 g/l of albumin, 0.40 g/l of myoglobin and 0.03 g/l of lysozyme were obtained from the separated solution withdrawn from the upper outlet 10 of the second unit 28.

0.41 g/l of albumin, 0.02 g/l of myoglobin and 0.04 g/l of lysozyme were obtained from the lower outlet 11 of the second unit 28.

Next, still another embodiment of the present invention, in which charged substances are separated by use of a plurality of electrophoretic separation apparatuses, will be described with reference to FIG. 6.

Figure 6:
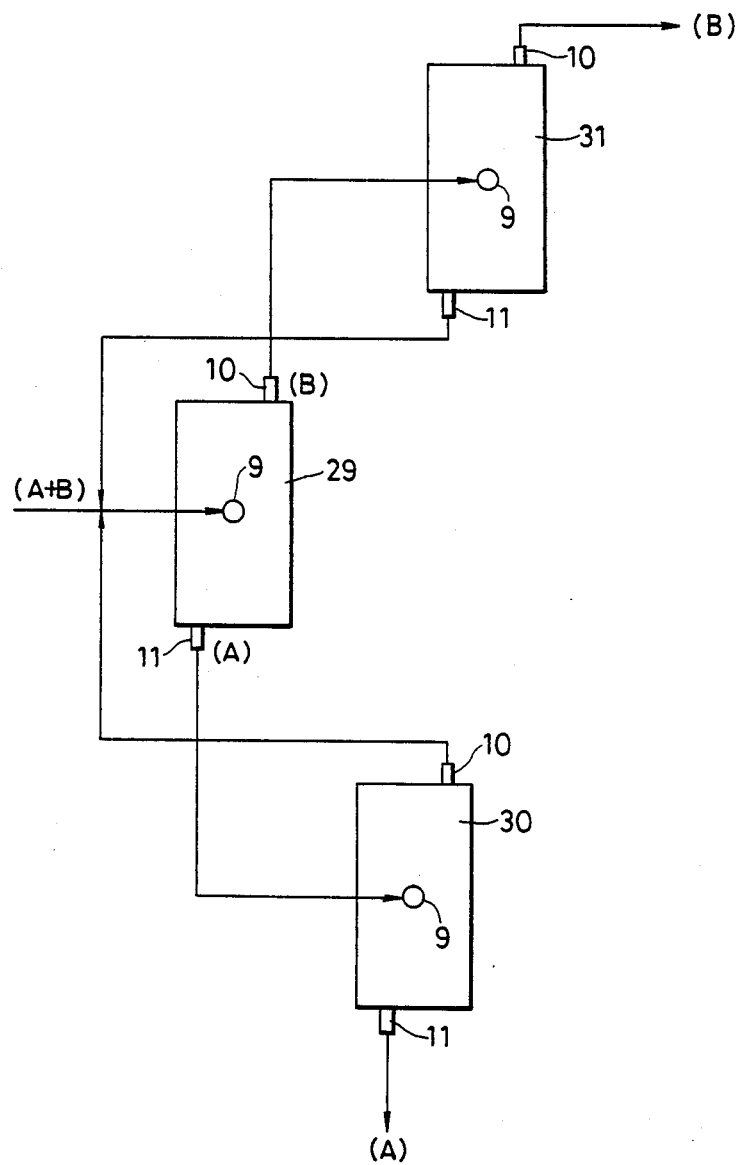
FIG. 6 is a block diagram showing still another embodiment of the present invention.

The embodiment shown in FIG. 6 uses three sets of electrophoretic separation apparatuses. Reference numerals 29, 30, 31 represent the apparatuses equivalent to the apparatus shown in FIG. 3, and the detailed description is omitted. These apparatuses will hereinafter be called simply the "units".

The unit 29 on the upstream side and the unit 30 on the downstream side are connected in series. In other words, the outlet 11 of the unit 29 is connected to the inlet 9 of the unit 30. The separated solution withdrawn from the outlet 10 of the unit 30 is fed back to the inlet of the upstream unit 29. On the other hand, the upstream unit 29 and the downstream unit 31 are connected in series. In other words, the outlet 10 of the unit 29 is connected to the inlet of the unit 31. The separated solution withdrawn from the outlet 11 of the unit 31 is fed back to the inlet of the upstream unit 29.

It will now be assumed that the substances to be separated are proteins A and B, and a mixed solution prepared by dissolving these proteins in the separation buffer is provided. It will also be assumed that the protein A in the mixed solution is charged negative, and the protein B, positive. The mixed solution is supplied into the electrophoresis cell from the inlet 9 of the unit 29, and the circulating flow of the mixed solution is formed inside the electrophoresis cell. The proteins A and B are then separated by applying a d.c. voltage between the electrodes. It will be assumed that inside the electrophoresis cell, the protein A moves towards the portion close to the outlet 11, while the protein B moves towards the portion close to the outlet 10. In this case, a separated solution containing a large proportion of the protein A is obtained from the outlet 11 of the unit 29, while a separated solution containing a large proportion of the protein B is obtained from the outlet 10 of the unit 29. However, the separated solution withdrawn from the outlet 11 contains not only the protein A but also a small amount of the protein B. Similarly, the separated solution withdrawn from the outlet 10 contains not only the protein B but also a small amount of the protein A. Therefore, a separation operation is further necessary in order to purify and obtain the proteins having a higher purity.

In the system shown in FIG. 6, the separated solution which is withdrawn from the outlet of the unit 29 and contains a large proportion of the protein A is supplied to the downstream unit 30, which effects the similar separation operation. As a result, a separated solution containing a larger proportion of the protein A is obtained from the outlet 11 of the downstream unit 30, and hence the protein A having higher purity can be obtained. A separated solution containing the proteins A and B can be obtained from the outlet 10 of the downstream unit 30. In this embodiment, this separated solution is fed back to the inlet of the upstream unit 29. In this manner, the recovery of the proteins can be improved, and the protein A having higher purity can be obtained from the outlet 11 of the unit 30. If the purity must be further improved, still another unit may be connected in series on the downstream side to make the separation operation.

The separated solution containing a large proportion of the protein B, which is withdrawn from the outlet 10 of the unit 29, is supplied to the downstream unit 31, where the same separation operation is carried out. As a result, a separated solutuion containing a larger proportion of the protein B, or the protein B having higher purity, can be obtained from the outlet 10 of the unit 31. Since the separated solution withdrawn from the outlet 11 of the unit 31 contains the proteins A and B, it is fed back to the upstream unit 29. Therefore, the recovery of the proteins can be improved. If the purity of the protein B obtained from the unit 31 is not sufficiently high, still another unit is connected in series downstream of the unit 31 to carry out the similar separation operation. Incidentally, the units 29, 30 and 31 are not particularly limited to the apparatus shown in FIG. 3, but may be those shown in FIGS. 2 and 4.

Next, an example of the separation of the charged substances using the system shown in FIG. 6 will be illustrated.

Example of separation by the system shown in FIG. 6:

The construction of each of the units 29, 30 and 31 is the same as that shown in FIG. 3.

The proteins to be separated were as follows:

| albumin (bovine) | isoelectric point PI = | 4.9 |
| myoglobin (horse) | isoelectric point PI = | 7.1–7.3 |

The separation buffer was a phosphoric acid buffer (pH=6.0, electric conductivity=25 ms/m). Each of the proteins was dissolved in the phosphoric acid buffer at a rate of 0.25 g/l to prepare a mixed solution, and this mixed solution was supplied to the electrophoresis cell of the unit 29 at a flowing velocity of 2.0 ml/min. A circulating flow of a velocity of 2.0 ml/min was formed by the circulating pump, and separated solutions were withdrawn from the outlets 10 and 11 at a rate of 1.0 ml/min, respectively. A current of 0.1 A (210 V) was applied between the electrodes. Since myoglobin was charged positive in the phosphoric acid of pH=6, it moved towards the portion close to the outlet 10 disposed near the negative electrode, and a myoglobin-rich separated solution was obtained from the outlet 10. On the other hand, since albumin was charged negative, it moved towards the portion close to the oulet 11 disposed near the positive electrode, and an albumin-rich separated solution was obtained from the outlet 11.

Subsequently, the myoglobin-rich separated solution was supplied to the downstream unit 31 at a rate of 1.0 m /min. The similar separation operations were conducted in the units 30 and 31. The separated solutions were withdrawn from the outlets 10 and 11 of the unit 30 at a flowing velocity of 0.5 m/l/min, respectively. The separated solutions were withdrawn from the outlets 10 and 11 of the unit 31 at a flowing velocity of 0.5 ml/min, respectively. The separated solution withdrawn from the upper outlet 10 of the unit 30 and the separated solution withdrawn from the lower outlet 11 of the unit 31 were fed back to the inlet of the unit 29. The separated solutions obtained from the lower outlet 11 of the unit 30 and from the upper outlet 10 of the unit 31 were analyzed with the result tabulated below.

| Place of withdrawal | albumin | myoglobin |
| --- | --- | --- |
| outlet 11 of unit 30 | purity: 93.8%<br>recovery ratio: 93% | — |
| outlet 10 of unit 31 | — | purity: 94.8%<br>recovery ratio: 92% |

As a result, it could be found that the system shown in FIG. 6 could separate the charged substances with high purity and high recovery ratio.

Figure 7:
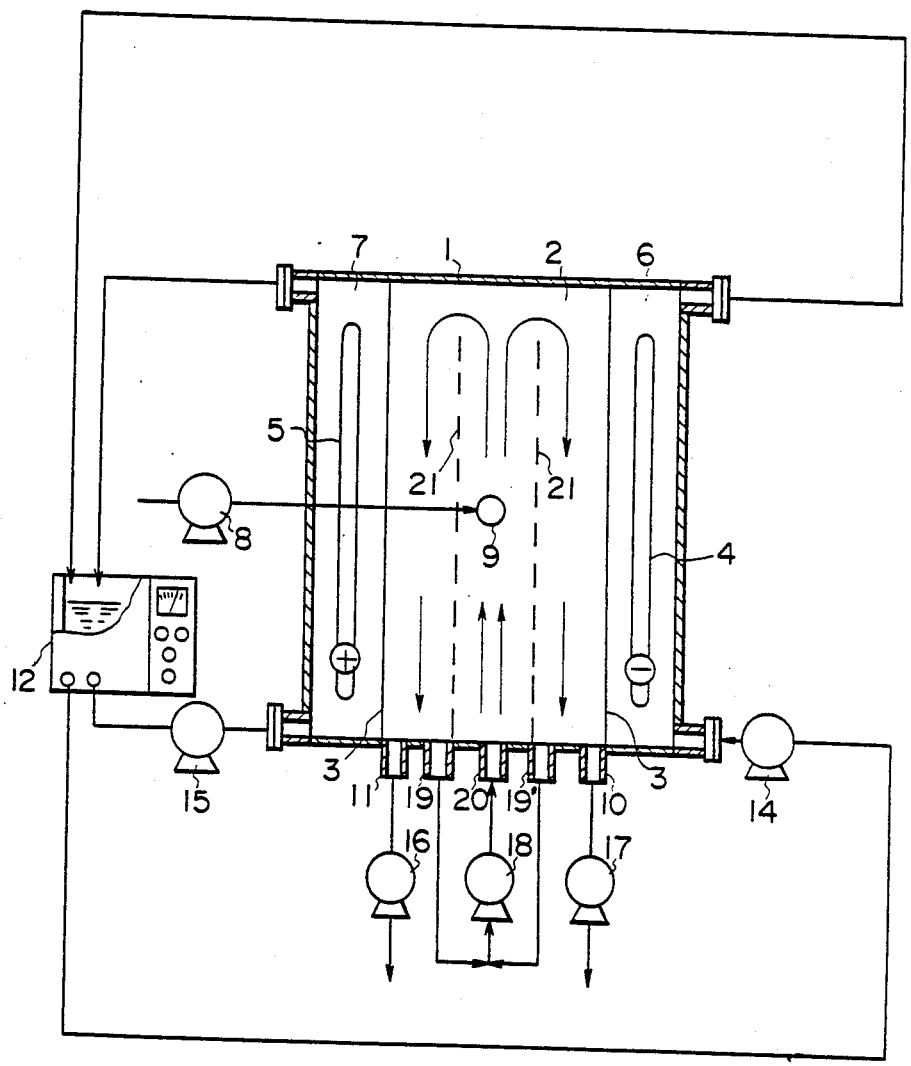
FIG. 7 is a schematic view showing another embodiment of the present invention.

Next, still another embodiment of the invention will be described with reference to FIG. 7. The apparatus shown in FIG. 7 resembles one shown in FIG. 3, but its structure of the electrophoresis cell is different. As shown in FIG. 7, electrophoresis cell 2 has two guide plates 21 which are parallel to the two membranes 3. These plates do not reach their top to the electrophoresis cell and divide the lower part of the cell into the three compartments.

The mixed solution is supplied into the center compartment through the inlet 9 and flows upward in the center compartment. Next the mixed solution is separated into two flow ways at the top of the center compartment, flows downward in each side compartment, the flow of the solution being indicated by the long arrow in the drawing. And the solution is withdrawn from the nozzle 19 and 19′, supplied to the circulating pump 18, and returned into the center compartment through the nozzle 20. Thereby the circulating flow of the mixed solution is formed.

And the separated solutions are withdrawn from the outlet 10 by the pump 17 and from the outlet 11 by the pump 16.

In the apparatus shown in FIG. 7, the mixed solution contained two kinds of proteins A and B, is supplied into the center compartment through the inlet 9. Isoelectric point of proteins A and B satisfy the relation $pI_A < pI_B$. And the pH of the buffer is adjusted to an intermediate value between these values. Then while the mixed solution in the electrophoresis cell 2 is being circulated by the circulating pump 18, and a d.c. voltage is applied across the electrodes 4 and 5.

The proteins A and B are separated and concentrated due to the circulating flow in cooperation with electrophoresis, that is, protein A is gathered near the outlet 11 and protein B near the outlet 10. In case of withdrawing the separated and concentrated protein from the electrophoresis cell, as higher concentrated protein has a higher specific density than the rest of the solution, it falls to the compartment bottom due to gravity.

So it is difficult to withdraw it from the upper outlet.

Therefore in this apparatus, the outlet 10 and 11 are disposed at the bottom of the each side compartments in the electrophoresis cell 2.

As described in the foregoing, the present invention eliminates the problem encountered when the mass separation treatment of charged substances is carried out, and can increase the processing quantity. The present invention can also improve the separation accuracy.

What is claimed is:

1. A free-flow electrophoretic separation method which comprises:

a step of supplying a solution containing charged substances to be separated into an electrophoresis cell at the center thereof, said cell having electrode cells at the both sides thereto and being partitioned from each of said electrode cells at said both sides with a membrane;

a step of causing said solution to flow as one main stream in a one direction at the center of said cell, causing said stream to divide into two partial streams and then for each partial stream to flow toward to one of said membranes, and causing the partial stream to then flow along a membrane in a direction opposite to said one direction at said center;

a step of applying a d.c. voltage to positive and negative electrodes located, respectively, in said electrode cells, to generate an electric field and to impose said electric field on said flowing solution thereby promoting flow and causing migration of the charged substance to at least one of said membranes; and a step of withdrawing said charged substances from said electrophoresis cell at an end of the flow along a membrane in the direction opposite to the one direction at said center.

2. A free-flow electrophoresis separation apparatus, which comprises:

electrode cells spaced from each other and having the positive and negative electrodes located therein, to each of which electrodes, a d.c. voltage is applied;

an electrophoresis cell which is located between said electrode cells and is partitioned from each of said electrode cells with a membrane;

an inlet for supplying a solution containing charged substances to be separated into the electrophoresis cell at the center thereof;

means for causing said solution to flow as a main stream in a one direction at said center, causing said stream flowing in said one direction to then divide into two partial streams, each partial stream flowing toward one of said membranes, causing each partial stream to then flow along a membrane in a direction opposite to said one direction at said center; and outlets for withdrawing a separated solution containing the charged substances in the partial streams, each flowing in said opposite directions, from said electrophoresis cell.

* * * * *